(12) United States Patent
Takeda et al.

(10) Patent No.: US 6,226,079 B1
(45) Date of Patent: May 1, 2001

(54) DEFECT ASSESSING APPARATUS AND METHOD, AND SEMICONDUCTOR MANUFACTURING METHOD

(75) Inventors: Kazuo Takeda, Tokorozawa; Makoto Ohkura, Fuchu; Seiichi Isomae, Hannou; Kyoko Minowa, Kokubunji; Muneo Maeshima, Mito; Shigeru Matsui, Hitachinaka; Yasushi Matsuda, Kodaira; Hirofumi Shimizu, Nakakoma-gun, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/161,393

(22) Filed: Sep. 29, 1998

(30) Foreign Application Priority Data

Sep. 29, 1997 (JP) .................................................. 9-264512

(51) Int. Cl.[7] ................................................. G01N 21/00
(52) U.S. Cl. ..................................... 356/237.2; 356/237.3
(58) Field of Search .................................... 356/237–239, 356/237.1–237.6, 337, 338, 340–343, 369, 364, 371, 430, 431, 445–448; 250/559.4, 559.41, 559.11, 559.16

(56) References Cited

U.S. PATENT DOCUMENTS

| | | | |
|---|---|---|---|
| 4,893,932 | * 1/1990 | Knollenberg | 356/369 |
| 5,032,734 | * 7/1991 | Orazio, Jr. et al. | 250/572 |
| 5,424,536 | * 6/1995 | Moriya | 250/225 |
| 5,581,346 | * 12/1996 | Sopori | 356/30 |
| 5,936,726 | * 8/1999 | Takeda et al. | 356/237.2 |
| 5,953,115 | * 9/1999 | Landers et al. | 356/237 |

FOREIGN PATENT DOCUMENTS

| | | |
|---|---|---|
| 5-264468 | 10/1993 | (JP) . |
| 6-50902 | 2/1994 | (JP) . |
| 7-294422 | 11/1995 | (JP) . |

* cited by examiner

Primary Examiner—Frank G. Font
Assistant Examiner—Michael P. Stafira
(74) Attorney, Agent, or Firm—Mattingly, Stanger & Malur, P.C.

(57) ABSTRACT

A defect assessing apparatus and method and a semiconductor manufacturing method for revealing the relationship between the size and depth of defects is disclosed. A detecting optical system is provided for detecting the intensity of scattered light from a defect generated by the shorter wavelength one of the light rays of at least two different wavelengths emitted from irradiating optical systems and that of scattered light from the defect generated by the longer wavelength one of same. A calculating means is provided for determining, from the scattered light intensity derived from the shorter wavelength ray and that derived form the longer wavelength ray, both detected by the detecting optical system, a value corresponding to the defect size and another value corresponding to the defect depth. A display means is provided for displaying a distribution revealing the relationship between defect size and defect depth on the basis of the value corresponding to the defect size and the value corresponding to the defect depth, both determined by the calculating means.

9 Claims, 11 Drawing Sheets

$\Delta t = \Delta L / V = \Delta L / (R d\omega / dt)$ $\Delta L$: LENGTH OF ARC BETWEEN $P_1$ AND $P_2$ $V$: LINEAR VELOCITY OF SCANNING $d\omega / dt$: ANGULAR VELOCITY

PRIOR ART

DEFECT ASSESSING APPARATUS AND METHOD, AND SEMICONDUCTOR MANUFACTURING METHOD

BACKGROUND OF THE INVENTION

The present invention relates to a defect assessing apparatus and method and a semiconductor manufacturing method to make possible detection and assessment of defects in silicon and other wafers including particles on the surface and crystal defects having an influence on semiconductor devices.

Prior Art

Defect measuring methods according to the prior art include irradiation with infrared rays, which can pass through silicon, and detection of the resultant scattered light. Such a measuring method requires measurement of the size and depth of each defect, because the impact of a defect varies with its size and depth.

One of the defect measuring techniques available according to the prior art is to cleave a silicon substrate, irradiate it with infrared rays passing through Si crystals in the direction of its cross section (the direction normal to the direction of the surface slope of the sample), and photograph optical images of defects as light points in the Si crystals. This method, called infrared scattering tomography, is described in detail in the *Journal of Crystal Growth*, Vol. 88 (1988), p. 332. This measuring technique, though it reveals the distribution of defects present in a minute area, requires cleaving of the sample and, being a destructive test, takes time to prepare the sample. As the sample is irradiated with a beam and scanned in the direction normal to the direction of detection, depth resolution can be achieved according to the diameter of the irradiating beam. The resolution is at most approximately the wavelength of the irradiating light (about 1 $\mu$m).

The Japanese Patent Laid-open No. Hei 5-264468 discloses a method by which the depth of each defect is determined by irradiating the sample with infrared rays obliquely, two-dimensionally observing a scattered image from within the sample with an infrared camera, and matching the depth of each part of the scattered image with the position in its field of vision. The depth resolution in this case is determined by optical imaging performance (focal depth), and approximately no finer than the product of the wavelength multiplied by the refractive index, i.e. at most 4 $\mu$m.

According to the prior art, disclosed in the Japanese Patent No. Hei 7-294422, laser beams differing in wavelength are brought to incidence on the same surface position of a silicon wafer and, as the penetration depth differs with the wavelength, the difference in the number of defects between the different wavelengths reveals the depth distribution of defects. Thus where, for instance, two different wavelengths are used, if a given defect can be detected by the wavelength of the greater penetration depth, the defect will be within this penetration depth, and if it cannot be detected by the other wavelength of the smaller penetration depth, the defect will be deeper than that penetration depth.

By another conventional method, disclosed in the Japanese Patent No. Hei 6-50902, for measuring defects on a semiconductor wafer surface, the wafer surface is irradiated with a laser beam. In this process, the wafer is rotated, and the scattered light from the wafer surface is condensed by a lens and detected by a detector. The apparatus to implement this process is provided with a frequency band-wise divider for dividing the obtained detection signals into a high frequency band, an intermediate frequency band and a low frequency band; a plurality of analog-to-digital (A/D) converters for digitizing the divided defect detection signals; and a plurality of memories for storing each defect at an address corresponding to its detected position as defect data. Each unit of defect data is processed by a data processing section, mapped on a printer band by band, and the type of defect is differentiated and assessed according to each mapped unit of defect data. This method is intended to differentiate defects by shape and size on the basis of the frequency band of scattered light detection signals generated in a pulse form over time. Measuring methods intended for the inspection of foreign matter on the surface, including this one, generally assesses the size of each piece of foreign matter on the surface according to the intensity of scattered light of one wavelength. When this principle is applied to the assessment of internal defect size, there arises the problem of impossibility to assessing the size of some defects because the scattered light intensity for defects even of the same size attenuates differently depending on their depth.

Devices in a large scale integrated (LSI) circuit are often formed in an area of not more than about 0.5 $\mu$m in depth from the silicon surface. Although defects in this area raise the ratio of device failure, defects in a deeper area are often unrelated to device failure. Therefore, the depth resolution of defect measurement should be at least 0.5 $\mu$m. Moreover, size assessment should be possible because the impact of a defect on a device differs with the size of the defect. A conventional wafer particle counters, which irradiates a wafer with light of a wavelength absorbable by the wafer and detects scattered light from a defect, can determine neither the size nor the depth because the intensity of scattered light varies with the depth and size of the defect. The method by which depth distribution is assessed from the difference in the number of defects according to the difference between wavelengths in penetration depth involves the problem that a correct result cannot be necessarily obtained because the detectable depth varies with the defect size. Furthermore, since defect size distribution varies with the depth, no correct measurement of defects is possible unless defect sizes are known as differentiated by depth.

SUMMARY OF THE INVENTION

An object of the present invention is to provide a defect assessing apparatus and method capable of revealing the relationship between the sizes and depths of defects.

Another object of the invention is to provide a defect assessing apparatus and method capable of measuring and assessing crystal defects arising in a maximum depth of about 0.5 $\mu$m in semiconductor substrates, such as silicon wafers, in terms of relationship between size and depth.

Still another object of the invention is to provide a semiconductor manufacturing method capable of clearly assessing the relationship between the sizes and depths of defects in semiconductor substrates, and enhancing the yield and reliability of semiconductors by building semiconductors into semiconductor substrates thereby assessed.

In order to achieve one or more of the above-stated objects, according to the invention, there are provided an apparatus and method for assessing any defect within a solid by irradiating the surface of the solid with light rays of a plurality of wavelengths and detecting scattered light from any defect at least in that solid, provided with: irradiating optical systems for irradiating with light rays of at least two different wavelengths differing in the depth of penetration into said solid; a detecting optical system for detecting the intensity of scattered light from a defect generated by the shorter wavelength one of the light rays of at least two different wavelengths emitted from the irradiating optical systems, and that of scattered light from the defect generated by the longer wavelength one of same; a calculating means (step) for figuring out, from the scattered light intensity deriving from the shorter wavelength ray and that deriving from the longer wavelength ray, both detected by the detecting optical system a value corresponding to the defect size and another value corresponding to the defect depth; and a display means (step) for displaying a distribution revealing the relationship between defect size and defect depth on the basis of the value corresponding to the defect size and the value corresponding to the defect depth, both figured out by the calculating means (step).

According to the invention, there are provided an apparatus and method for assessing any defect within a solid by irradiating the surface of the solid with light rays of a plurality of wavelengths and detecting scattered light from any defect at least in that solid, provided with: irradiating optical systems for irradiating with light rays of at least two different wavelengths differing in the depth of penetration into said solid; a detecting optical system for detecting the intensity of scattered light from a defect generated by the shorter wavelength one of the light rays of at least two different wavelengths emitted from the irradiating optical systems, and that of scattered light from the defect generated by the longer wavelength one of same; a calculating means (step) for figuring out, from the scattered light intensity deriving from the shorter wavelength ray and that deriving from the longer wavelength ray, both detected by the detecting optical system, a value corresponding to the defect size and another value corresponding to the defect depth; and a display means (step) for displaying a depth distribution as differentiated by defect size on the basis of the value corresponding to the defect size and the value corresponding to the defect depth, both figured out by the calculating means (step).

According to the invention, there are provided an apparatus and method for assessing any defect within a solid by irradiating the surface of the solid with light rays of a plurality of wavelengths and detecting scattered light from any defect at least in that solid, provided with: irradiating optical systems for irradiating with light rays of at least two different wavelengths differing in the depth of penetration into said solid; a detecting optical system for detecting the intensity of scattered light from a defect generated by the shorter wavelength one of the light rays of at least two different wavelengths emitted from the irradiating optical systems, and that of scattered light from the defect generated by the longer wavelength one of same; a calculating means (step) for figuring out, from the scattered light intensity deriving from the shorter wavelength ray and that deriving from the longer wavelength ray, both detected by the detecting optical system, a two-dimensional distribution; and a display means (step) for displaying a distribution revealing the relationship between defect size and defect depth on the basis of the two-dimensional distribution figured out by the calculating means (step).

According to the invention, there are provided an apparatus and method for assessing any defect within a solid by irradiating the surface of the solid with light rays of a plurality of wavelengths and detecting scattered light from any defect at least in that solid, provided with: irradiating optical systems for irradiating with light rays of at least two different wavelengths differing in the depth of penetration into said solid; a detecting optical system for detecting the intensity of scattered light from a defect generated by the shorter wavelength one of the light rays of at least two different wavelengths emitted from the irradiating optical systems, and that of scattered light from the defect generated by the longer wavelength one of same; a calculating means (step) for figuring out, from the scattered light intensity deriving from the shorter wavelength ray and that deriving from the longer wavelength ray, both detected by the detecting optical system, a two-dimensional distribution; and a display means (step) for displaying a depth distribution as differentiated by defect size on the basis of the two-dimensional distribution figured out by the calculating means (step).

According to the invention, there are also provided an apparatus and method for defect assessment as described above, in whose irradiating optical systems one of the two or more different wavelengths is at least three times as great in the depth of penetration of the solid as the other(s).

According to the invention, there is also provided an apparatus and method for defect assessment as described above. In whose display means (step) anything to allow perception of the solid surface is displayed According to the invention, there is also provided an apparatus and method for defect assessment as described above, in whose display means (step) a defect distribution is displayed in which values proportional to the logarithm of the scattered light intensity deriving from the longer wavelength are plotted on the X axis and values proportional to the logarithm of the scattered light intensity deriving from the shorter wavelength from the defect are plotted on the Y axis.

According to the invention, there is also provided an apparatus and method for defect assessment as described above, in whose display means (step) a defect distribution is displayed in which values proportional to the sixth root of the scattered light intensity deriving from the longer wavelength are plotted on the X axis and values proportional to the logarithm of the scattered light intensity deriving from the shorter wavelength from the defect are plotted on the Y axis.

According to the invention, there is also provided an apparatus and method for defect assessment as described above, in whose display means (step) a defect distribution is displayed in which values proportional to the sixth root of the scattered light intensity deriving from the longer wavelength are plotted on the X axis and the logarithms of their ratios to the scattered light intensity deriving from the shorter wavelength from the defect are plotted on the Y axis.

According to the invention, there is also provided an apparatus for assessing any defect within a solid by irradiating the machined surface of the solid with light rays of a plurality of wavelengths and detecting scattered light from any defect at least in that solid, having a means for displaying an a display unit defect information to distinguish between a defect due to the machining of said solid surface or one within the solid According to the invention, there is also provided a defect assessing apparatus for measuring any defect within or on the surface of a semiconductor wafer, having a means for displaying on a display unit defect information to distinguish between a defect due to the machining of the surface of the wafer and one within the wafer.

According to the invention, there is also provided a defect assessing apparatus as described above, wherein the defect information displayed on the display unit is a depth distribution as differentiated by defect size.

According to the invention, there is also provided a defect assessing apparatus for detecting and assessing any defect within or on the surface of a solid by Irradiating the solid surface with light absorbable by the solid and measuring the resultant scattered light, having a means for deriving the depth of defects as differentiated by defect size and displaying the result on a display unit.

According to the invention, there is also provided a defect assessing apparatus for detecting and assessing any defect within or on the surface of a solid by irradiating the solid surface with light absorbable by the solid and measuring the resultant scattered light, having a means for displaying on a display unit the sizes of defects as differentiated by depth.

According to the invention, there is also provided a defect assessing method for detecting and assessing any defect within or on the surface of a solid by irradiating the solid surface with light absorbable by the solid and measuring the resultant scattered light, whereby the depths of defects are derived as differentiated by defect size and the result is displayed on a display unit According to the invention, there is also provided a defect assessing method for detecting and assessing any defect within or on the surface of a solid by irradiating the solid surface with light absorbable by the solid and measuring the resultant scattered light, whereby the sizes of defects are displayed on a display unit as differentiated by depth.

According to the invention, there is also provided a semiconductor manufacturing method whereby the surface of a semiconductor substrate is irradiated with light absorbable by the semiconductor substrate, the resultant scattered light obtained from the semiconductor substrate is measured, the sizes of defects are displayed on a display unit as differentiated by depth on the basis of the measured scattered light intensities to assess the defects on the surface of or within the semiconductor substrate, and a semiconductor is built into a semiconductor substrate found free of trouble on the basis of the assessment.

According to the invention, there is also provided a defect measuring method using an epitaxial-wafer as standard sample for measuring the defect depth.

As hitherto described, the above-described configuration makes it possible to measure and assess crystal defects of a maximum depth of about 0.5 μm in a semiconductor substrate, such as a silicon wafer, in terms of relationship between size and depth, prevent a large scale integrated (LSI) semiconductor from being built into a faulty substrate on that basis, and thereby enhance the yield and reliability of LSI semiconductors.

The above-described configuration also makes it possible, when manufacturing semiconductors, any troublesome defects, including those within the sample (solid), in detail and, if the sample is faulty, to facilitate identification of the cause of fault, thereby enabling a remedy to be promptly and readily taken and the yield of the sample to be enhanced significantly.

The above-described configuration further makes it possible, when building a large scale integrated (LSI) circuit into a silicon wafer, to enhance the yield and reliability of satisfactory products, free from faults in metal oxide semiconductor (MOS) transistors constituting the LSI circuit. Failures in MOS transistors are typically due to the insulation destruction of gate oxide films and excess leak currents from junctions. Most of these failures in MOS transistors are either directly or indirectly caused by crystal defects in the silicon substrate. Thus, in an LSI circuit manufacturing process, if any crystal defect exists in the surface area of the silicon substrate which is to be converted by oxidation into a silicon oxide film, a structural defect will be formed in the silicon oxide film, inviting insulation destruction when the LSI circuit operates. Or if a crystal defect is present in the depletion layer of a junction, there will arise a large quantity of leak current. Thus, formation of any crystal defect in the surface area in which elements are formed in the silicon substrate is an undesirable phenomenon, because it invites a fault in the MOS transistor. However, the present invention, which can reveal the relationship between the sizes and the depth of defects, makes it possible to accurately assess crystal defects present in the surface areas of the semiconductor substrate, thereby reducing faults in and increasing the reliability of large scale integrated semiconductors.

DETAILED DESCRIPTION OF THE PREFERRED EMBODIMENTS

Apparatuses and methods for defect assessment, which are preferred embodiments of the present invention, will be described below with reference to drawings.

Figure 1:
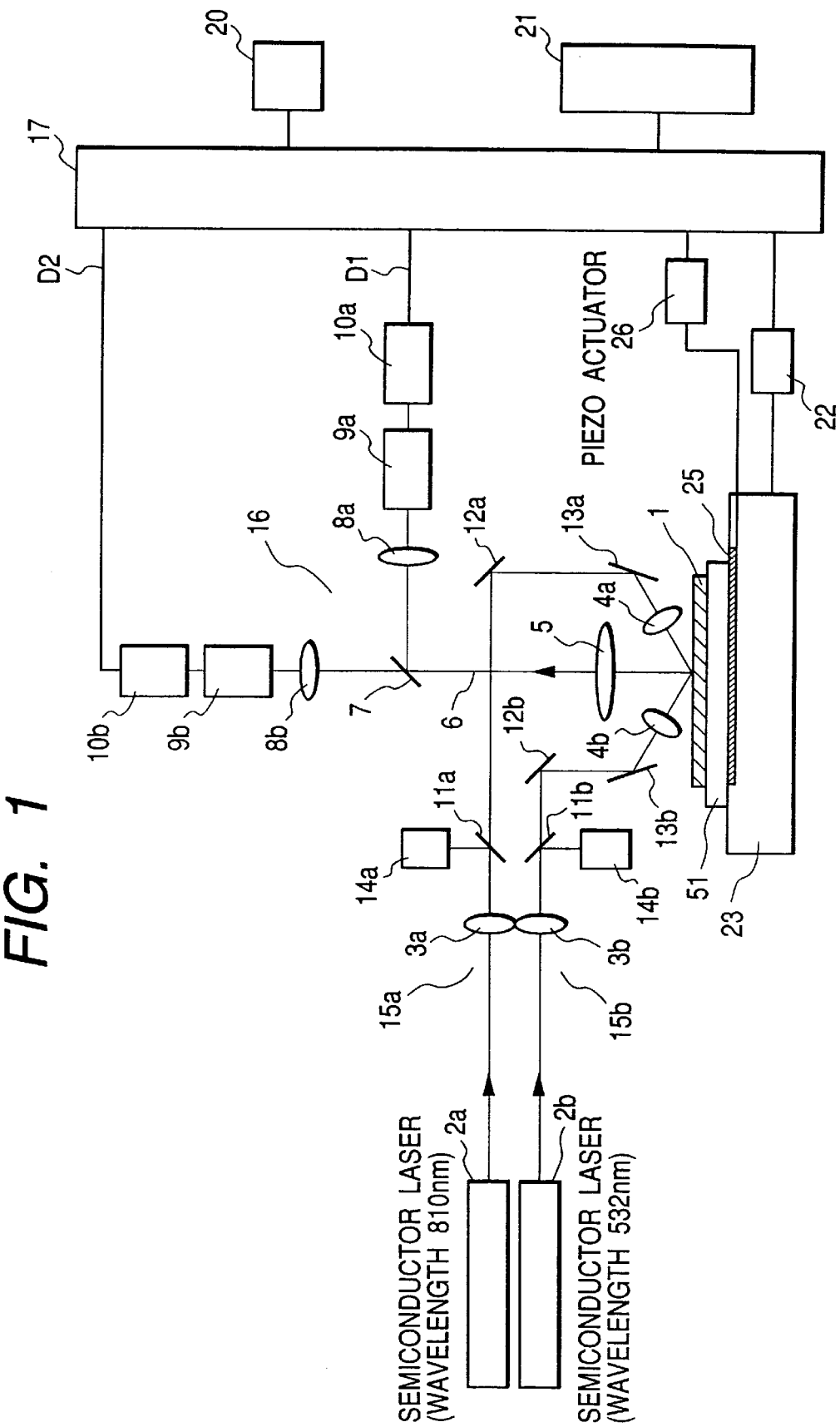
FIG. 1 is a diagram schematically illustrating a defect measuring apparatus, which is a preferred embodiment of the present invention.

FIG. 1 is a diagram schematically illustrating a defect measuring apparatus, which is a preferred embodiment of the present invention. In the figure, reference numeral 1 denotes a sample for measuring crystal defects, such as oxygen deposits ($SiO_2$ particles) and inversions, arising in an area to a maximum depth of about 0.5 µm in terms of relationship between size and depth, and the sample consists of a semiconductor substrate, such as a silicon wafer or a GaAs wafer. The need for a depth resolution of no less fineness than 0.5 µm for this defect measurement is due to the circumstance that devices are often formed in an LSI circuit in the area of up to about 0.5 µm from the substrate surface. Thus, while formation of defects in this area would raise the proportion of faulty devices, defects in a deeper area are often irrelevant to device faults.

Reference numerals 2a and 2b denote light sources for emitting light rays of wavelengths λ1 and λ2 of which one has a penetration depth Γ1 which is at least three times as great as the penetration depth Γ2 of the other, and they may consist of semiconductor laser beam sources for example. The light sources 2a and 2b may be either at least two separate light sources or a single light source capable of simultaneously emitting light rays of at least two different wavelengths λ1 and λ2. Or else, they may be a single variable-wavelength light source. Reference numerals 15a and 15b denote irradiating optical systems for irradiating the sample 1 with light rays of wavelengths λ1 and λ2, and they respectively consist of lenses 3a and 3b for shaping the light rays emitted from the light sources 2a and 2b into substantially parallel beams; mirrors 12a and 12b; mirrors 13a and 13b for irradiating the surface of the sample with the light rays of wavelengths λ1 and λ2 at an incident angle θ; and condensing lenses 4a and 4b for condensing the light rays of wavelengths λ1 and λ2 on parts on the surface of the sample close to each other and irradiating them with the condensed light rays. The reason why the light rays of wavelengths λ1 and λ2 are focused with the condensing lenses 4a and 4b on mutually close parts (points P1 and P2 in FIG. 2) on the surface of the sample 1 is that any interference between the two irradiating light rays could be prevented thereby. Where a single light source emitting the light rays of at least two different wavelengths λ1 and λ2 simultaneously is used, it is desirable that its output be separated into the two wavelengths and the light rays of wavelengths λ1 and λ2 be focused by the respective irradiation optical systems 15a and 15b on mutually close parts (points P1 and P2 in FIG. 2) on the surface of the sample 1 to irradiate it. The length of the arc between two points P1 and P2 is represented by ΔL. Reference numerals 14a and 14b denote sensors for monitoring the intensities of the irradiating light rays emitted from the light sources 2a and 2b and reflected by half mirrors 11a and 11b. The light sources 2a and 2b are controlled so as to keep constant the intensities of the irradiating light rays monitored by the sensors 14a and 14b. This serves to maintain the intensities I1 and I2 of the light rays irradiating the sample 1 at constant levels. Incidentally, said sensors 14a and 14b may be positioned behind the mirrors 12a and 12b to detect the intensities of the irradiating light rays having passed the mirrors 12a and 12b.

Figure 2:
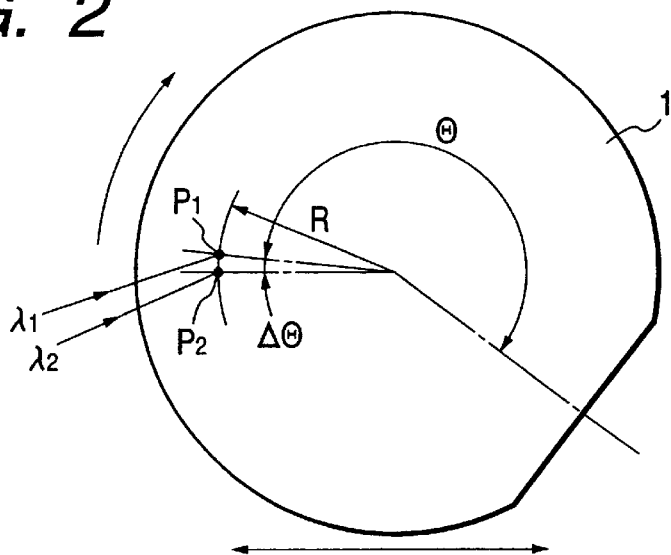
FIG. 2 shows how a sample is irradiated with light rays of two different wavelengths in the apparatus illustrated in FIG. 1.

Reference numeral 23 denotes a stage assembly on which the sample 1 is placed and irradiated with the light rays, and mainly consists of a rotary stage and a sliding stage, driven by a driver 22 in accordance with control instructions from a computer 17. The rotary stage is intended to rotate the sample 1, and the shifting stage, to shift the sample 1 in the radial direction. This configuration of the stage assembly 23 consisting of the rotary stage and the sliding stage enables the irradiating light rays to scan the sample 1 spirally. While the above-described configuration supposes the sample 1 to be moved for scanning by the irradiating light rays, the irradiating optical systems and the detecting optical system may as well be moved to scan the sample 1. However, moving the stage assembly 23 is more desirable for control ease. The stage assembly 23 is provided with a rotary encoder (not shown) for detecting the rotary displacement of the rotary stage and a parallel moving encoder (not shown) for detecting the sliding displacement of the sliding stage so that the coordinates of a sample fixing Jig 51, i.e. coordinates (radius R and rotary angle Θ) of detection of any defect on the sample 1 as shown in FIG. 2, can be monitored and entered into the computer 17. Where the angular speed (dω/dt) is kept constant irrespective of the radius R, the time difference Δt between signals S1 and S2 is in inverse proportion to R. Or where the linear velocity (V) is kept constant irrespective of the radius r, Δt is constant.

Reference numeral 16 denotes a detecting optical system for separating scattered light rays generating from defects either on the surface of or inside the sample according to the irradiating wavelength, detecting them with optical detectors 9a and 9b for the different wavelengths, and converting them into electric signals D1 (S1) and D2 (S2), and this system consists of an object glass 5; a wavelength separating optical system 7, consisting of a dichroic mirror or the like, for separation according to the irradiating wavelength; condensing lenses 8a and 8b for condensing each of the scattered light rays separated by the wavelength separating optical system according to the irradiating wavelength; and photodetectors 9a and 9b for receiving the scattered light rays condensed by the condensing lenses 8a and 8b and supplying scattered light intensity signals S1 and S2. The wavelength separating optical system 7 may consist of a half mirror for branching light rays into two optical paths; filters, one of which is installed on each optical path, for intercepting scattered light rays deriving from the wavelengths λ2 and λ1.

Reference numerals 10a and 10b denote combinations of an amplifier and an A/D converter each, which amplify the scattered light intensity signals D1 and D2 supplied by the photodetectors 9a and 9b, respectively, and convert them into digital signals as their respective outputs.

As a means to detect the height of the surface of the sample 1 during defect measurement, a gap sensor (not shown), for example, is provided in the vicinity of the object glass 5, and variations in the surface height of the sample 1 are kept within the focal depth of the object glass 5 by slightly moving up and down the sample fixing jig 51 which fixes the sample 1 by controlling a servo mechanism utilizing a piezo element 25 driven by a piezo element driver 26 in accordance with control instructions from the computer 17 obtained on the basis of information on the surface height of the sample 1 detected by this means.

Figure 3A:
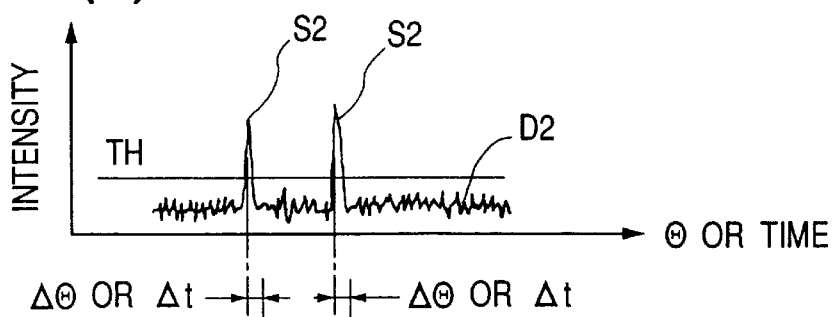
FIGS. 3(A) and 3(B) comprise diagrams showing scattered light intensity signals D1 and D2 obtained by detecting scattered light rays resulting from the irradiation of the sample with light rays of two different wavelengths with the apparatus illustrated in FIG. 1.
Figure 3B:
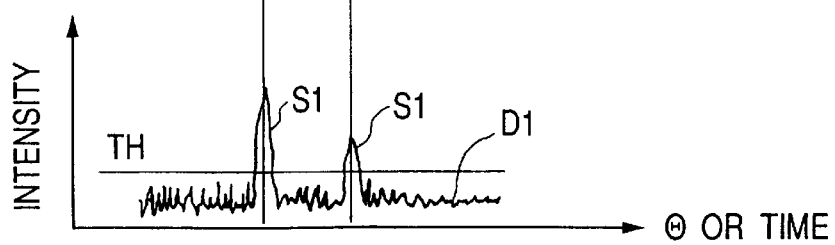

The computer 17 sets a threshold TH as shown in FIG. 3 to avoid erroneous detection of any noise component in regard to the scattered light intensity signal D2 for a specific wavelength $\lambda 2$ out of the two wavelengths entered from the amplifier-A/D converter 10b. On the basis of a trigger signal generated when the scattered light intensity signal D2 surpasses the threshold TH, the computer 17 takes in the peak value, for example, of the digitized scattered light intensity signal S2 together with the coordinates of the detected position (radius R and rotary angle $\Theta+\Delta\Theta$)) to store them in either an internal memory or an external memory unit 21 and, in regard to the scattered light intensity signal D1 for a specific wavelength $\lambda 1$ out of the two wavelengths entered from the amplifier-A/D converter 10a, takes in the peak value, for example, of the digitized scattered light intensity signal S1, generated behind the peak position (central position) of the scattered light intensity signal S2 by the rotary angle $\Delta\Theta$ on the basis of said trigger signal, as the coordinates of the detected position (radius R and rotary angle $\Theta+\Delta\Theta$) to store them in either the internal memory or the external memory unit 21. Essentially, these actions are taken, with a view to preventing optical interference, to cause the irradiating optical systems 15a and 15b to irradiate mutually close parts (points P1 and P2) on the surface of the sample 1 with the light rays of the wavelengths $\lambda 2$ and $\lambda 1$, respectively. Further by setting the threshold TH, it is made possible to prevent any fluctuation in scattered light intensity (noise component) generating from the surface of the sampler from being detected as a signal indicating a defect. Moreover, as the relationship between the peak position (central position) of the scattered light intensity signal S2 and that of the scattered light intensity signal S1 is determined by $\Delta L$, it is made possible to figure out the intensity value of the scattered light intensity signal S2 and that of the scattered light intensity signal S1 from the same coordinate position (radius R, rotary angle $\Theta+\Delta\Theta$).

Next, the computer 17 calculates a value corresponding to the defect size from the digitized intensity of scattered light from a defect deriving from the wavelength $\lambda 1$, having a greater penetration depth $\Gamma 1$, which is stored in the internal memory or the external memory unit 21, derives a value corresponding to the depth position Z of the defect by using the scattered light ray intensities based on the two wavelengths $\lambda 2$ and $\lambda 1$, which are stored in the internal memory or the external memory unit 21, and causes two-dimensional displaying of defects in depth distribution by size to be accomplished on a display unit 20. The present invention is particularly characterized by the two-dimensional displaying of defects in depth distribution as differentiated by size on the display unit 20. This aspect will be described in greater detail elsewhere in this specification.

Next will be described actions in the aforementioned apparatus. Thus, a semiconductor laser beam of the wavelength $\lambda 1$ of, for instance, 810 nm emitted from the light source 2a and a second harmonic generation (SHG) of a YAG laser beam of the wavelength $\lambda 2$ of, for instance, 532 nm emitted from the light source 2b are parallelized in a p-polarized direction with respect to the surface of the sample 1 by the lenses 3a and 3b, condensed by the mirrors 12a and 12b and the lenses 4a and 4b, and irradiate the surface of the sample 1. In this process, measurement is done with the irradiating positions P2 and P1 staggered by a distance a few times as long as the irradiating beam diameter (about 5 $\mu$m) so that, as the sample 1 is scanned, the beam of 532 nm in wavelength irradiate any defect earlier than the beam of 810 nm in wavelength. A defect is detected by taking in the two signals S2 and S1 deriving from the wavelength $\lambda 2=532$ nm and the wavelength $\lambda 1=810$ nm, respectively, only when the scattered light intensity signal (D2) deriving from the wavelength $\lambda 2=532$ nm surpasses a certain preset threshold TH, it being provided that the threshold TH is so set as not to let any variation in the intensity of scattered light (noise component) generated from the surface of the sample 1 be detected as a signal.

As the surface of the sample 1 is scanned by an irradiating area, each of any crystal defects contained in the sample, such as oxygen deposits ($SiO_2$ particles) and inversions, is detected by the detection of Rayleigh scattered light generated from the defect at the moment the defect in the sample passes the irradiating area. Scattered light rays 6 are condensed with the object glass 5, undergo separation by the wavelength separating optical system 7 into scattered light rays of 810 nm and 532 nm in wavelength, condensed by the lenses 8a and 8b, respectively, and detected by photodetectors 9a and 9b as separated according to wavelength. The detection signals are amplified by the amplifiers 10a and 10b, digitized by the A/D converters 10a and 10b, and taken into the computer 17. On the other hand, the computer 17, while using the driver 22 to scan the stage 23 in the rotary direction ($\Theta$direction) and the radial direction (R direction) and monitoring the coordinates (R, $\Theta$) on the sample detected by the rotary encoder and the parallel moving encoder, measures scattered light, and takes in coordinates (R, $\Theta+\Delta\Theta$) at the moment of generation of scattered light from a defect together with the scattered light intensity signals D2 and D1. During the measurement, the surface height of the sample 1 is detected by, for instance, a gap sensor (not shown) arranged close to the object glass 5, and the piezo element driver 26 is driven on the basis of this detected information on the surface height of the sample to keep the variations in the surface height of the sample 1 within the focal depth of the object glass 5 with the servo mechanism using the piezo element 25.

Next will be explained the principle, according to the present invention, of measurement and assessment of crystal defects arising in a sample, such as a silicon wafer or a GaAs wafer, in terms of relationship between size and depth.

Thus, where n and k are the refractive index and the attenuation rate, respectively, of the sample material at a wavelength $\lambda$, the penetrating depth $\Gamma$ at which the amplitude of the irradiating light becomes 1/θ of the value of the surface is given by the following Equation 1.

$$\Gamma=\lambda/(2\pi k) \qquad \text{Equation 1}$$

Therefore, the intensity of irradiating light having come incident from in the air upon a substance at an incident angle θ at a depth Z from the surface, considering that its refraction angle θ2 in the sample is arcsin((sinθ)/n), is attenuated by $\exp[(-2Z\Gamma)\cdot\cos(\arcsin((\sin\theta)/n))]=\exp[(-2Z/\Gamma)\cdot\cos\theta 2]$ compared with the intensity on the surface.

Figure 4:
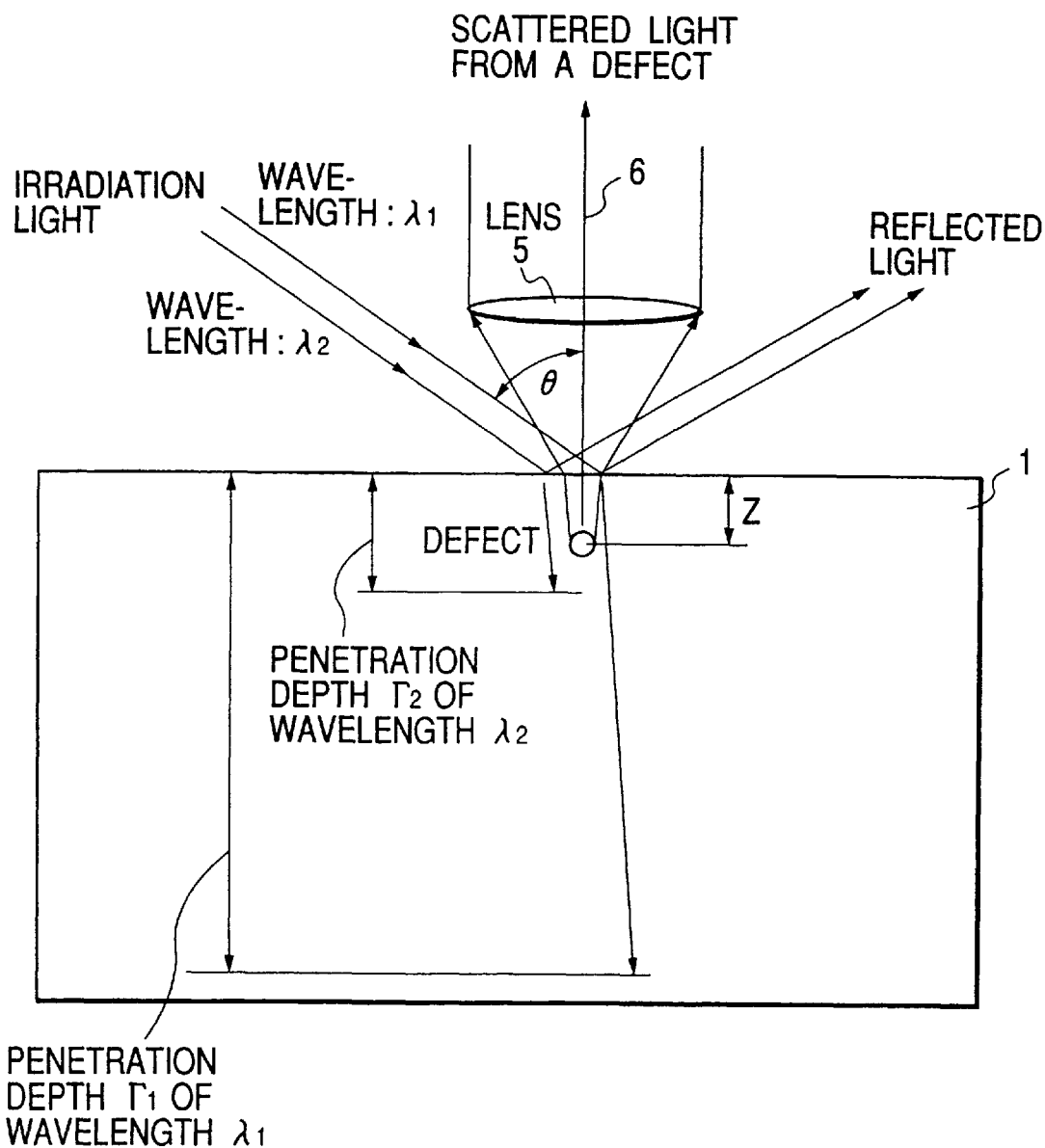
FIG. 4 is a diagram for explaining the principle of defect measurement by detecting scattered light rays resulting from the irradiation of the sample with light rays of two different wavelengths according to the invention.

Next will be considered a case in which, as illustrated in FIG. 4, light comes incident from in the air on the surface of the sample 1 at an incident angle θ, and that irradiating light detects, at a certain solid angle with the object glass 5, light scattered by a defect within the sample 1 toward the surface of the sample 1. Where, with respect to that detection solid angle, σ, I, Ti and Ts are respectively the integrated scattered cross sectional area of the defect, irradiating light intensity, transmissivity of the irradiating light within the sample at an incident angle θ, and transmissivity of the scattered light from the defect from within the sample into the atmosphere, the intensity of scattered light S from the defect positioned at a depth Z from the surface of the substance can be represented by the following Equation 2, which takes into account both the attenuation of the irradiating light and that of the scattered light.

$$S=Ti \cdot Ts \cdot I \cdot \sigma \cdot \exp[(-2Z/\Gamma)(1+1/\{\cos(\arcsin((\sin \theta)/n))\})]= Ti \cdot Ts \cdot I \cdot \sigma \cdot \exp[(-2Z/\Gamma)(1+1/\{\cos\theta 2\})] \quad \text{Equation 2}$$

The following relationships of Equation 3 and Equation 4 will hold where. in regard to the wavelengths λ1 and λ2, n1 and n2 are the respective refractive indices of the sample; Γ1 and Γ2, the penetration depth; I1 and I2, the intensities of irradiating light; S1 and S2, the measured intensities of scattered light; σ1 and σ2, the integrated scattered cross sectional areas: Ti1 and Ti2, the transmissivities of irradiating light; and Ts1 and Ts2, the transmissivities of scattered light.

$$S1=Ti1 \cdot Ts1 \cdot I1 \cdot \sigma 1 \cdot \exp[-(2Z/\Gamma 1)(1+1/\{\cos(\arcsin((\sin\theta)/n1))\})] \quad \text{Equation 3}$$

$$S2=Ti2 \cdot Ts2 \cdot I2 \cdot \sigma 2 \cdot \exp[-(2Z/\Gamma 2)(1+1/\{\cos(\arcsin((\sin\theta)/n2))\})] \quad \text{Equation 4}$$

where Γ1>Γ2.

The depth Z where the defect is positioned can be represented by the following Equation 5 because of the relationships of Equations 3 and 4.

$$Z=C1 \cdot \ln[C2 \cdot I(S1/S2) \cdot (\sigma 2/\sigma 1)] \quad \text{Equation 5}$$

where C1 and C2 consist of device constants and the optical constants of the sample, and are defined by the following Equations 6 and 7.

$$C1=1/[(2/\Gamma 2)(1+1/\{\cos(\arcsin((\sin \theta)/n2))\})-(2/\Gamma 1)(1+1/\{\cos(\arcsin((\sin \theta)/n1))\})] \quad \text{Equation 6}$$

$$C2=(I2/I1) \cdot ((Ti2 \cdot Ts2)/(Ti1 \cdot Ts1)) \quad \text{Equation 7}$$

Since C1 and C2 are device constants, if the value of (S1/S2)·(σ2/σ1) is found, the depth Z where the defect is positioned can be known from the relationship of Equation 5.

Here S1/S2 is the ratio of the signal intensities of scattered light measured of the defect, and can be computed by the computer 17 from the measurements detected by the photodetectors 9a and 9b. In this connection, a method to calculate σ2/σ1 will be described below.

Since σ2 and σ1 are calculated from the grain size of the defect by applying the Mie scattering theory (e.g. M. Born and E. Wolf, *Principles of Optics* 3, Japanese translation published by Tokai University Press, 1975, pp. 902–971) and the theory on scattering in absorptive media (an article by Peter Chylek, *Journal of the Optical Society of America*, Vol. 67, pp. 561–563), the principle of grain size measurement will be explained first.

Now, the scattered light intensity signal S1 from a defect existing within the penetration depth Γ2, detected by the scattered light intensity signal S2, is considered. Where Γ1>>Γ2 holds, the attenuation factor of this S1 due to depth takes on a value of 1, which is negligible, because the depth position Z of the detected defect satisfies the condition of Z<Γ2. This relationship will be quantitatively explained below.

It is considered to what extent the attenuation of signal intensity S1 due to depth should be restrained in order to measure the defect size with a tolerance of, for instance, no more than 10%. Since the defect is no more than 0.1 μm in most cases of actual measurement, a phenomenon of scattering due to a defect can be treated as a case of Rayleigh scattering in which the intensity S of scattered light is proportional to the sixth power of the grain size d and to the minus fourth power of the wavelength λ as indicated by Equation 8.

$$S=A \cdot d^6/\lambda^4 \quad \text{Equation 8}$$

where A is a proportional constant.

Figure 5:
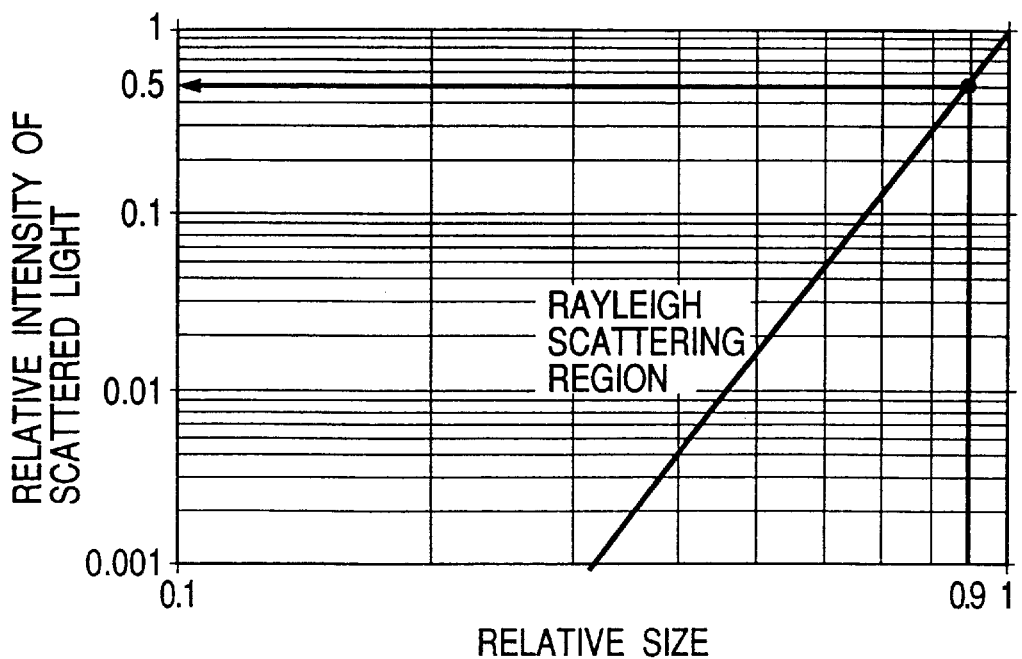
FIG. 5 is a diagram for explaining the relationship between the accuracy of grain size measurement and that of scattered light measurement.

FIG. 5 shows the relationship between the accuracy of grain size measurement and that of scattered light intensity measurement in a Rayleigh scattering region where the grain size d is sufficiently smaller than the wavelength Γ1/Γ2>3. This is a relationship in which the scattered light intensity S is proportional to the sixth power of the grain size d, because the grain size d is sufficiently smaller than the wavelength λ to permit treatment as a case of Rayleigh scattering.

Therefore it is seen from the relationship shown in FIG. 5 that, in order to secure a tolerance of grain size measurement not more than 10%. the tolerance of scattered light intensity measurement should be 50%. This is understood from the fact that, when the relative grain size shrinks from 1 to 0.9, the relative scattered light intensity decreases from 1 to 0.5.

Figure 6:
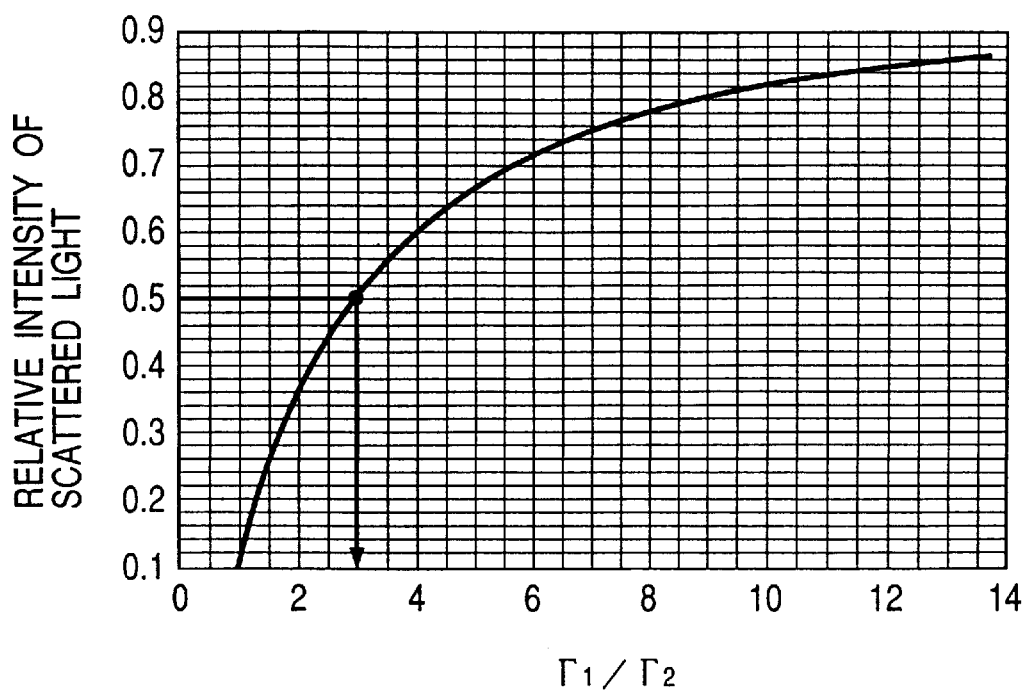
FIG. 6 is a diagram illustrating the rate of attenuation dependent on the ratio between the two wavelengths in penetration depth and on the depth of scattered light intensity for determining the grain size.

Incidentally, with regard to the signal S1 from a defect detected at a penetration depth of no more than Γ2, substitution of Z=Γ2 into Equation 3 gives a relationship between Γ1/Γ2 and the relative scattered light intensity based on the following Equation 9 as shown in FIG. 6.

$$S1=Ti1 \cdot Ts1 \cdot I1 \cdot \sigma 1 \cdot \exp[-(2\Gamma 2/\Gamma 1)(1+1/\{\cos(\arcsin((\sin\theta)/n1))\})] \quad \text{Equation 9}$$

This gives Γ1/Γ2>3 as the necessary condition for keeping the rate attenuation due to depth within 50% (relative scattered light intensity of no less than 0.5).

At any rate, the condition of Γ1/Γ2>3 is determined, because of the aforementioned relationship of Equation 1, is determined by the relationship between the wavelengths λ1 and λ2 of the two irradiating light rays on one hand and the attenuation rate k of the sample substance to be irradiated on the other.

Where the combination of the wavelength λ1=810 nm and the wavelength λ2=532 nm, described with reference to the aforementioned embodiment, is used, the penetration depth ratio Γ1/Γ2 is about 10, well satisfying the condition (Γ1/Γ2>3) to secure the above-stated grain size measurement tolerance of no more than 10%.

Or, in the case of Rayleigh scattering, σ2/σ1 becomes a quantity dependent not on the grain size of the defect but only on the irradiating wavelength as indicated by the following Equation 10.

$$\sigma 2/\sigma 1=(\lambda 1/\lambda 2)^4 \quad \text{Equation 10}$$

Therefore, by substituting Equation 10 given above into Equation 5, the equation for computation of the defect depth Z by the computer 17 is simplified as indicated by Equations 11 and 12 below.

$$Z=C1 \cdot \ln(S1/S2)+C0 \quad \text{Equation 11}$$

where C0 is a device constant as indicated by the following equation.

$$C0=C1=\ln[C2 \cdot (\lambda 1/\lambda 2)^4] \quad \text{Equation 12}$$

Further, the grain size d to be computed by the computer 17 can be represented by Equation 13 because S1 is proportional to the sixth power of d.

$$\ln(d) = (1/6)\ln(S1) + C3 \qquad \text{Equation 13}$$

where C3 is the function of the wavelength $\lambda 1$, the angle of detection (the solid angle of detection by the object glass 5) and the irradiation intensity I1, and is a device constant.

As explained above, the computer 17 can compute the defect depth Z on the basis of the Equation 11 above by computing the ratio (S1/S2) of scattered light intensity signals attributable to the defect, and the defect size (grain size) d on the basis of the Equation 13 above from the scattered light intensity signal (S1).

Next will be explained the two-dimensional displaying of defect distribution on the display unit 20. Since defects in actual silicon or GaAs are often found in the Rayleigh scattering region, the following explanation will use Equation 11 with regard to the measurement of the defect depth Z and Equation 13 with regard to the measurement of the defect size (grain size) d.

Incidentally, the following Equation 14 can be derived from Equation 11.

$$Z = C1 \cdot \ln(S2) + C1 \cdot \ln(S1) + C0 \qquad \text{Equation 14}$$

First will be described, with reference to FIG. 7, a first example of depth distribution displaying, as differentiated by grain size, by the computer 17 on the display unit 20. Here, the two-dimensional displaying of defects (Plot 1), where $\ln(S1) = X$ and $\ln(S2) = Y$ is supposed because of the relationship of Equation 14, conforms to the following Equation 15.

$$Y = X + (C0 - Z)/C1 \qquad \text{Equation 15}$$

Figure 7:
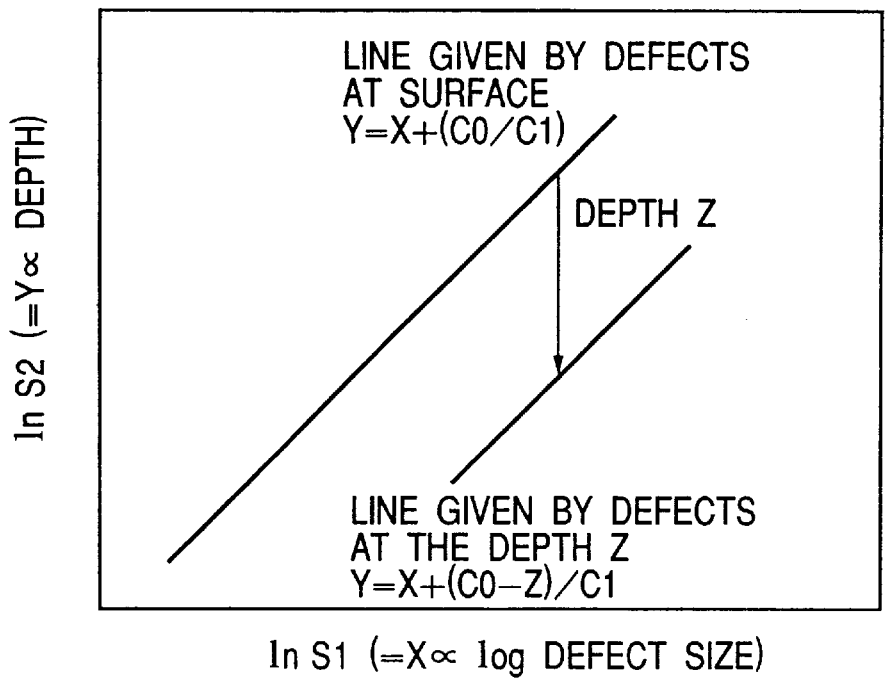
FIG. 7 is a diagram for explaining the principle of the system of Plot 1, which is a first example of two-dimensional displaying on the display unit of defects consisting of depth distribution as differentiated by grain size.

Therefore the computer 17 can perform two-dimensional displaying of and assess the defect as illustrated in FIG. 7 (Plot 1) by setting the value of ln(S1) (corresponding to defect size) proportional to log (defect size) as the horizontal axis (X axis) and the value of ln(S2) proportional to the defect depth Z as the vertical axis (Y axis) on the screen of the display unit 20.

Incidentally, in the two-dimensional displaying of the defect as shown in FIG. 7 (Plot 1), the surface line whose depth Z equals 0 can be represented by the following Equation 16 by reason of Equation 13. To add, the surface line representing the surface of the sample displayed together with the two-dimensional displaying (Plot 1) of the defect given on the screen of the display unit 20 and represented by the following Equation 16 need not be a line. It may as well be a sign, a difference in shade or a color as far as it can make the surface of the sample perceivable.

$$Y = X + (C0/C1) \qquad \text{Equation 16}$$

It is further seen that defects having a depth Z are distributed from the line of Equation 16 representing the surface toward a line shifted in parallel in the minus direction of Y by Z/C1.

Then, the computer 17 computes the value proportional to log (defect size) (a value corresponding to defect size) by finding the logarithm of the peak value S1 of the scattered light intensity signal representing the defect, obtained by applying the threshold TH to the digitized scattered light intensity signal D1 supplied by the A/D converter 10a, computes the value proportional to the defect depth Z (a value corresponding to defect depth) by finding the logarithm of the peak value S2 of the scattered light intensity signal representing the defect, obtained by applying the threshold TH to the digitized scattered light intensity signal D2 supplied by the A/D converter 10b, and can perform two-dimensional displaying (Plot 1) of and assess depth distribution as differentiated by grain size by plotting these computed values of the X and Y axes in coordinate positions, consisting of the X and Y axes set on the screen of the display unit 20.

Next will be described, with reference to FIG. 8, a second example of depth distribution displaying, as differentiated by grain size, by the computer 17 on the display unit 20. In this case, the two-dimensional displaying of defects (Plot 2), where $-\ln(S1/S2) = Y$ and $\ln(S1) = X$ are supposed by reason of the relationship of Equation 14, conforms to the following Equation 17.

$$Z = -C1 \cdot Y + C0 \qquad \text{Equation 17}$$

Figure 8:
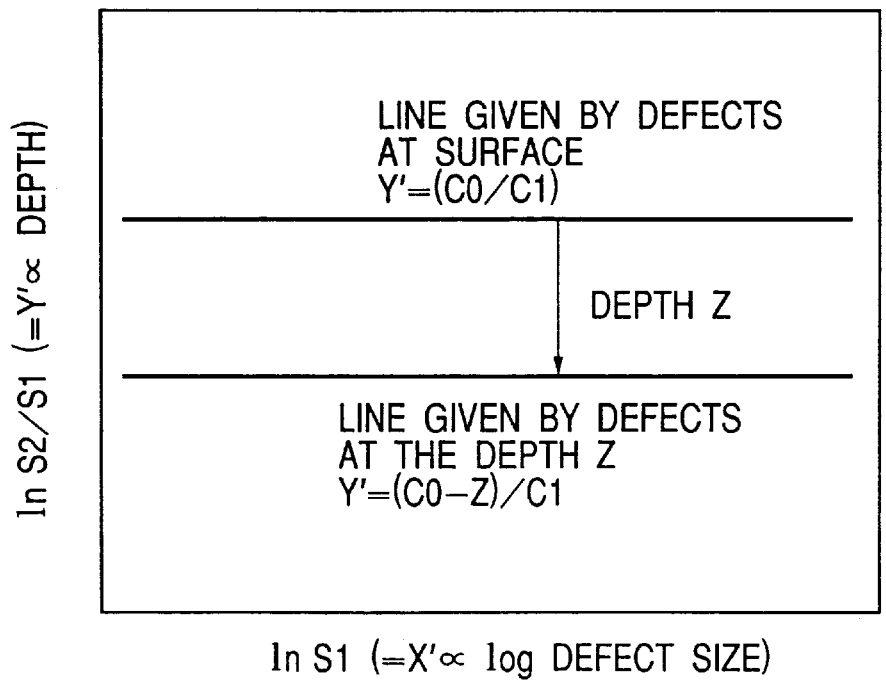
FIG. 8 is a diagram for explaining the principle of the system of Plot 2, which is a second example of two-dimensional displaying on the display unit of defects consisting of depth distribution as differentiated by grain size.

Therefore the computer 17 can perform two-dimensional displaying of and assess the defect as illustrated in FIG. 8 (Plot 2) by setting the value of ln(S1) (corresponding to defect size) proportional to log (defect size) as the horizontal axis (X axis) and the value of ln(S2/S1) proportional to the defect depth Z as the vertical axis (Y axis) on the screen of the display unit 20.

Incidentally, in the two-dimensional displaying of the defect as shown in FIG. 8 (Plot 2), the surface line whose depth Z=0 can be represented by the following Equation 18 by reason of Equation 17. To add, the surface line representing the surface of the sample displayed together with the two-dimensional displaying (Plot 2) of the defect given on the screen of the display unit 20 and represented by the following Equation 18 need not be a line. It may as well be a sign, a difference in shade or a color as far as it can make the surface of the sample perceivable.

$$Y = C1/C0 \qquad \text{Equation 18}$$

Further, the line on which defects having a depth Z are distributed can be represented by $Y = (C0 - Z)/C1$.

Then, the computer 17 computes the value proportional to log (defect size) (a value corresponding to defect size) by finding the logarithm of the peak value S1 of the scattered light intensity signal representing the defect, obtained by applying the threshold TH to the digitized scattered light intensity signal D1 supplied by the A/D converter 10a, computes the value proportional to the defect depth Z (a value corresponding to defect depth) by finding the logarithm of the ratio (S2/S1) between the peak value S2 of the scattered light intensity signal representing the defect, obtained by applying the threshold TH to the digitized scattered light intensity signal D2 supplied by the A/D converter 10b, and the peak value S1 of said scattered light intensity signal, and can perform two-dimensional displaying (Plot 2) of and assess depth distribution as differentiated by grain size by plotting these computed values of the X and Y axes in coordinate positions, consisting of the X and Y axes set on the screen of the display unit 20.

From the foregoing description, it may be seen that two-dimensional displaying by the system of Plot 1 (first example) has the advantage of allowing simultaneous confirmation and assessment of the relative intensities of signals and the depth distribution of defects as differentiated by size as the coordinate axes corresponding to the scattered light intensities, but it involves the problem of slanted displaying of the surface line.

Two-dimensional displaying of the system of Plot 2 (second example) has the advantage of displaying the depth horizontally and thereby allowing intuitive assessment, but it involves the problem of some difficulty in perceiving the relative degrees of signal intensity.

In the two-dimensional graphs of FIG. 7 and FIG. 8, the computer 17 can display on the display unit 20 graduations proportional to the defect size (grain size) by setting values proportional to the sixth root of S1 as the X axis representing values corresponding to defect sizes, calculating the sixth root of S1 and plotting the resultant value as the X coordinate.

The aforementioned device constants, such as C1 and C0, are determined in advance by the computer 17 using a plurality each of standard samples for grain size and standard samples for depth. Thus, a standard sample of a plurality of grain sizes, to whose surface a plurality of known kinds of standard particles having grain sizes of d0 and d1 are adhered, is fitted to the sample fixing jig 51. and placed on the stage 23; a scattered light intensity signal D1 corresponding to the wavelength $\lambda 1$ and a scattered light intensity signal D2 corresponding to the wavelength $\lambda 2$ are detected: and the computer 17 computes the values of $\ln(S1(d0))$ and $\ln(S1(d1))$ or of the sixth root of $(S1(d0))$ and that of $(S1(d1))$ corresponding to the known grain sizes d0 and d1, respectively, and at the same time the values of $\ln(S2(d0))$ and $\ln(S2(d1))$ or those of $\ln(S2(d0))/S1(d0))$ and $\ln(S2(d1))/S1(d1))$ corresponding to the known grain sizes d0 and d1, respectively. The surface line, as it relates to the horizontal axis in FIG. 9 or 10. is set on the basis of the relationship between these computed values of $\ln(S1)$ or of the sixth root of $(S1)$ and the values of $\ln(S2)$ or $\ln(S2/S1)$ corresponding to the known grain sizes d0 and d1, respectively.

Figure 9:
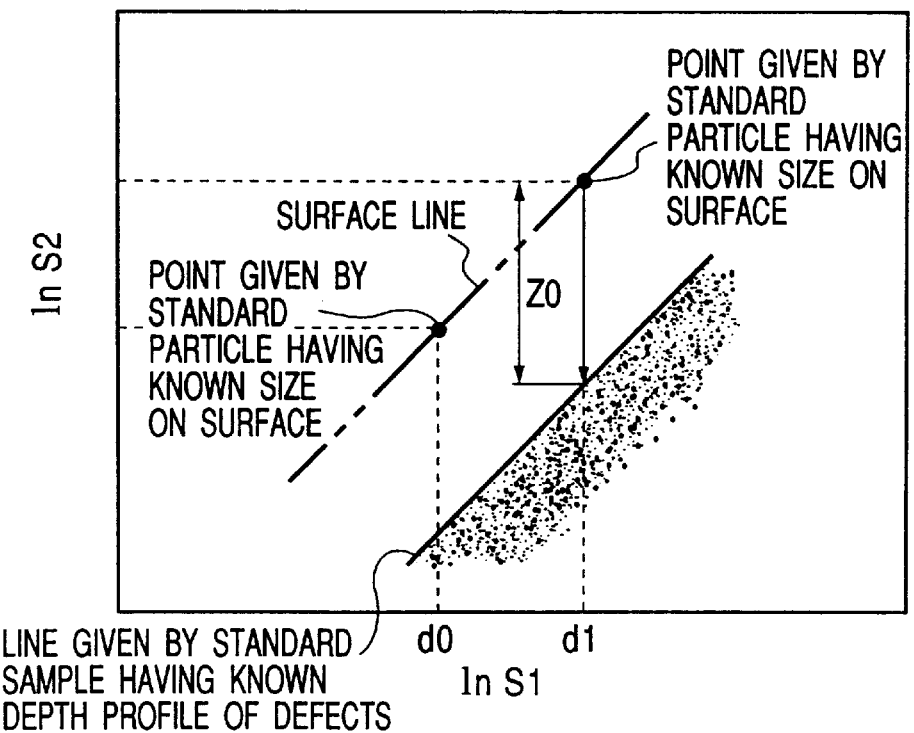
FIG. 9 is a diagram for explaining how the values (graduations) on the horizontal axis (representing values corresponding to defect size) and on the vertical axis (representing values corresponding to depth) are set in the system of Plot 1, which is the first embodiment.
Figure 10:
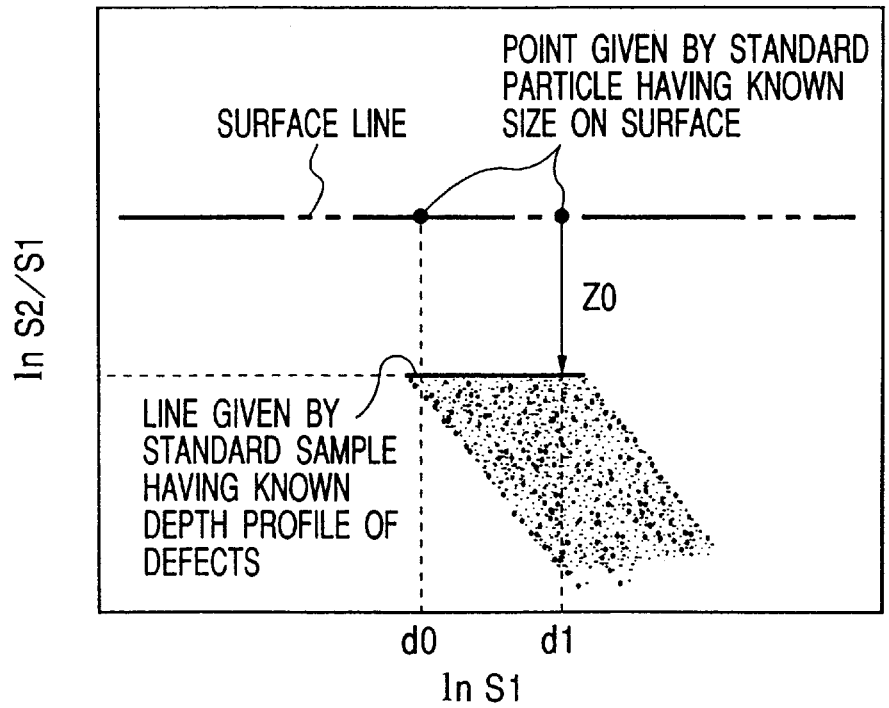
FIG. 10 is a diagram for explaining how the values (graduations) on the horizontal axis (representing values corresponding to defect size) and on the vertical axis (representing values corresponding to depth) are set in the system of Plot 2, which is the second embodiment.

Further, a standard depth sample having no defect on the surface, in which a layer Z0 of a known thickness is formed, is fitted to the sample fixing jig 51, and placed on the stage 23; a scattered light intensity signal D1 corresponding to the wavelength $\lambda 1$ and a scattered light intensity signal D2 corresponding to the wavelength $\lambda 2$ are detected; and the computer 17 computes the values of $\ln(S2)$ or that of $\ln(S2/S1)$. The values for the vertical axis in FIG. 9 or 10 are set on the basis of these computed values of $\ln(S2)$ or of $\ln(S2/S1)$ corresponding to the known thickness Z0.

As described above, the computer 17 determines the device constants including C1 and C0, calibrates them with the devices, and registers them in the external memory unit 21. Since the intensities I1 and I2 of the irradiating light rays emitted by the light sources 2a and 2b, respectively, are kept constant, this calibration need not be done frequently, but may be done only on the occasions of maintenance and inspection.

For the calibration procedure referred to above, polystyrene particles of known grain sizes d0 and d1 adhered to the wafer surface are appropriate as standard particles for grain size, and an epitaxial wafer whose epitaxial layer has a known depth Z0 is appropriate as a standard sample for depth. The reason why an epitaxial wafer can be a standard sample for depth is the extreme low density of defects in the epitaxial layer compared with the density of defects in the substrate underneath the epitaxial layer, which makes the wafer usable as a standard sample of the depth distribution of defect density.

Figure 11:
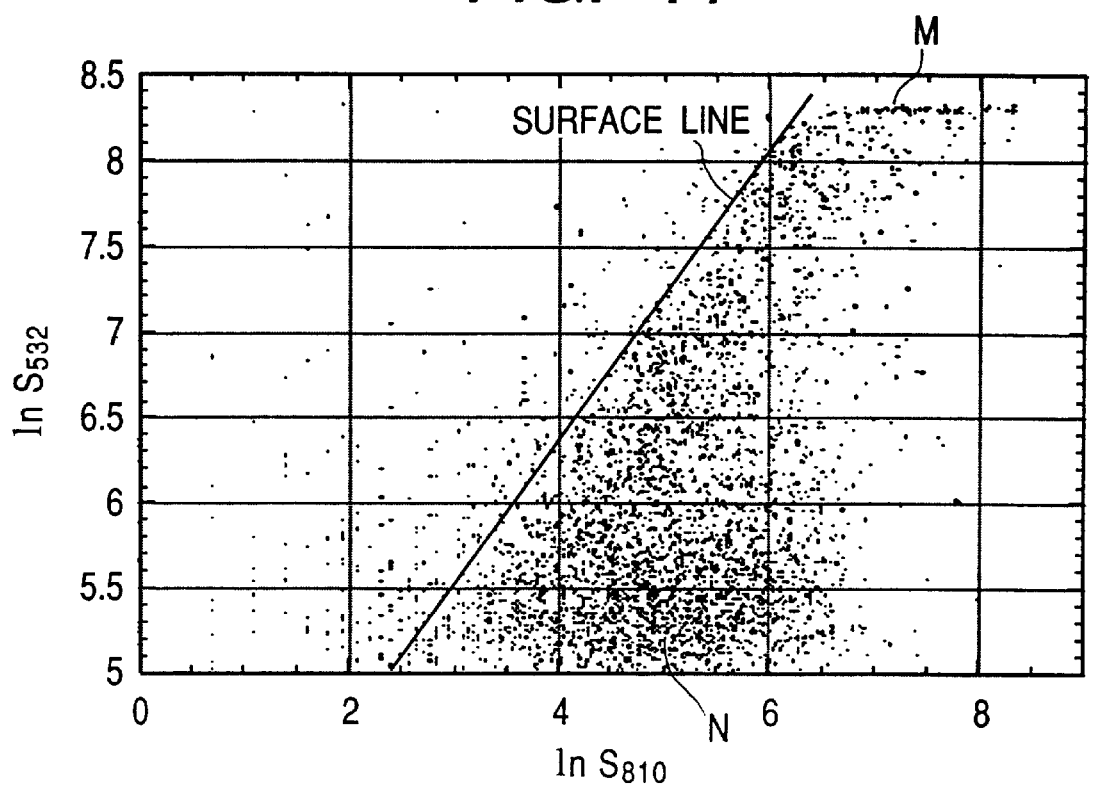
FIG. 11 is a diagram illustrating an example of displaying of defects in untreated CZ silicon according to the system of Plot 1, which is the first example.

FIG. 11 illustrates how the measurements of defects in untreated CZ silicon are displayed on the screen of the display unit 20 according to the above-described system of Plot 1 (the first example). If the surface line is also displayed, it will be easier to recognize the position of the sample surface in the X-Y coordinate system. As the penetration depth of the wavelength $\lambda 1=810$ nm is about 10 times as great as that of the wavelength $\lambda 2=532$ nm, the attenuation of the light of the 810 nm wavelength can be ignored within the penetration depth of the 532 nm wavelength. Therefore, the size of the scattering agent (defect) can be directly figured out from the intensity S1 of the 810 nm scattered light. In this diagram, defects are two-dimensionally represented, with the horizontal axis representing the logarithm of the intensity of the 810 nm scattered light (lnS1), and the vertical axis, that of the intensity of the 532 nm scattered light (lnS2). In this graph, by reason of Equation 13, the horizontal axis can be regarded as representing a quantity proportional to the logarithm of the defect size (grain size), and the vertical axis, a quantity proportional to the defect depth because the intensity of scattered light attenuates logarithmically with the defect depth Z. These correlations between (lnS1) and the defect size and between (lnS2) and the defect depth Z can be grasped by the computer 17 during calibration with standard samples. It is therefore made possible to represent directly the defect size values or values corresponding to the defect size on the horizontal axis (X axis) and directly the defect depth values or values corresponding to the defect depth on the vertical axis (Y axis).

Figure 12:
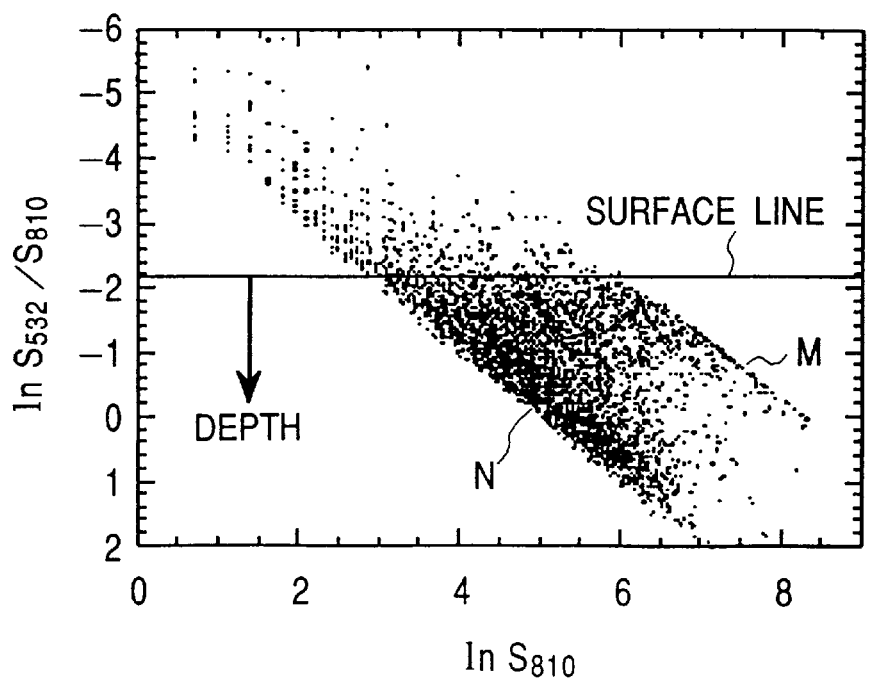
FIG. 12 is a diagram illustrating an example of displaying of defects in untreated CZ silicon according to the system of Plot 2, which is the second example.

FIG. 12 illustrates how the computer 17 displays the same data on the display unit 20 according to the system of plot 2 (the second example). In this case again, if the surface line is also displayed, it will be easier to recognize the position of the sample surface in the X-Y coordinate system.

Incidentally, M and N in FIG. 11 correspond to respectively the same reference letters in FIG. 12.

Figure 13:
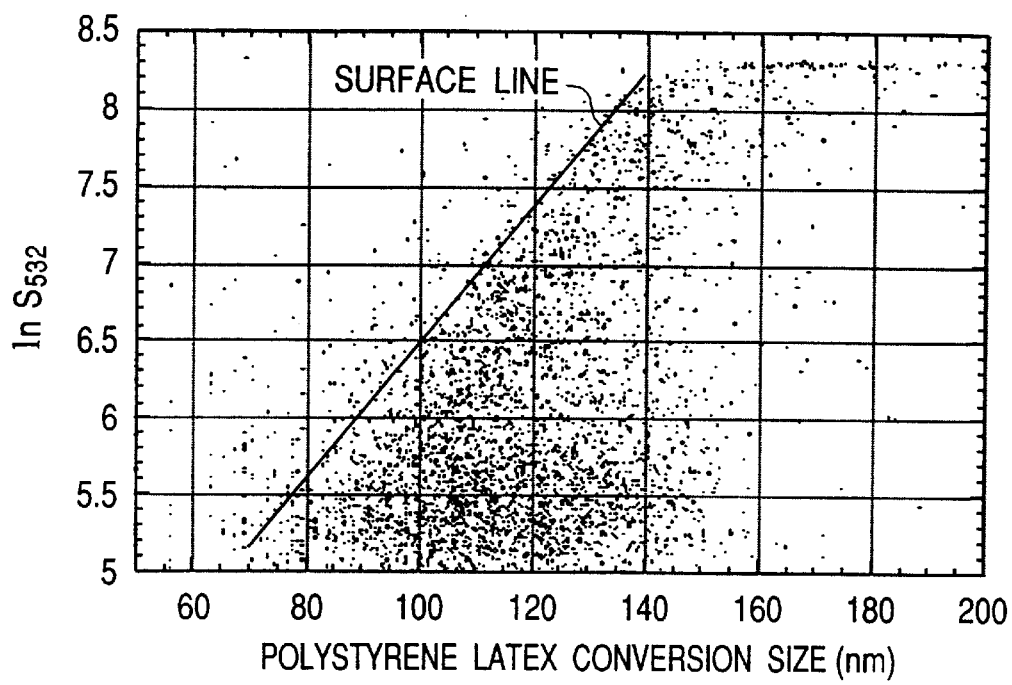
FIG. 13 is a diagram illustrating an example of displaying wherein polystyrene latex conversion sizes (defect sizes) are represented by the horizontal axis of the plot in FIG. 11.

FIG. 13 is a diagram illustrating an example of displaying wherein defect sizes (polystyrene latex conversion sizes) are represented by the horizontal axis of the depth distribution as differentiated by grain size, shown in FIG. 11. A polystyrene latex conversion size is obtained, when calibration is conducted using the aforementioned standard samples for grain size, on the basis of the size of polystyrene particles adhered to the wafer surface, generating a scattered light intensity equal to the intensity of 810 nm scattered light from a defect. Thus, where the horizontal axis (X axis) represents the quantity equal to the sixth root of the intensity S1 of the 810 nm scattered light, the scale of this horizontal axis may be graduated, when calibration is conducted using the aforementioned samples for grain size, with the peak position of grain size distribution, obtained by measuring a wafer to whose surface are adhered polystyrene particles of a known grain size, being supposed to be the known polystyrene latex conversion size. Representation on the horizontal axis shown in FIG. 12 can be accomplished in the same way. The depth graduations (on the vertical axis) were determined by assuming the depth, at which the density abruptly varies in the defect depth distribution measured for an epitaxial wafer whose epitaxial layer depth Z0 is, for instance, 0.3 $\mu$m, when the graduations are calibrated using the aforementioned standard samples for depth.

Figure 14:
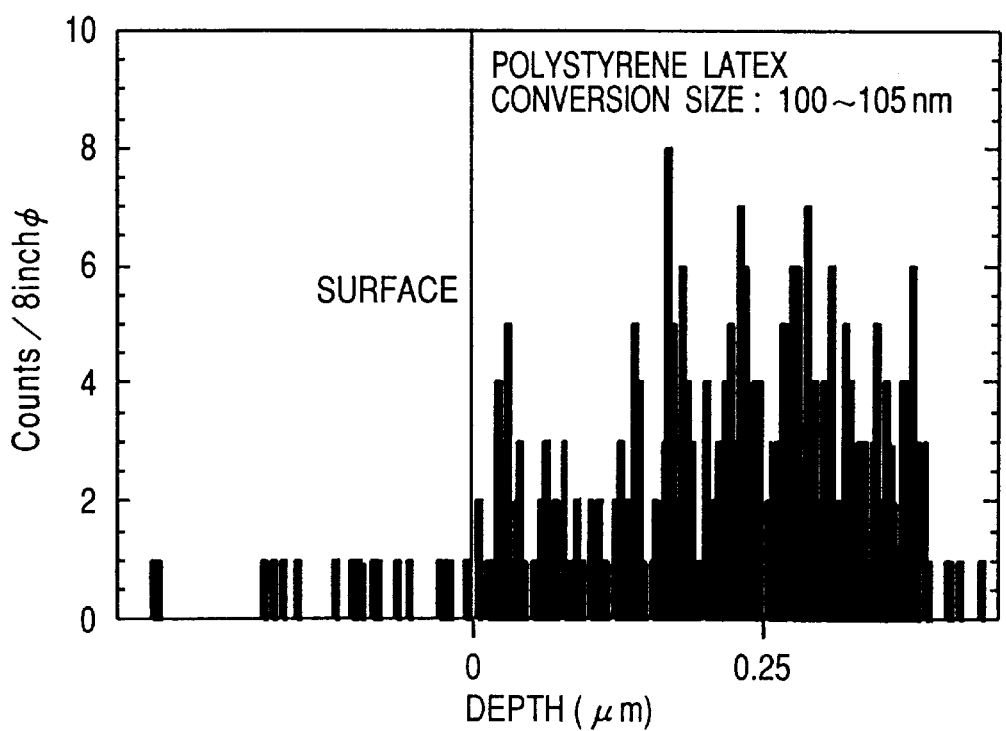
FIG. 14 is a diagram illustrating an example of displaying of depth distribution in a limited defect size range in the plot of FIG. 11, FIG. 12 or FIG. 13.
Figure 15:
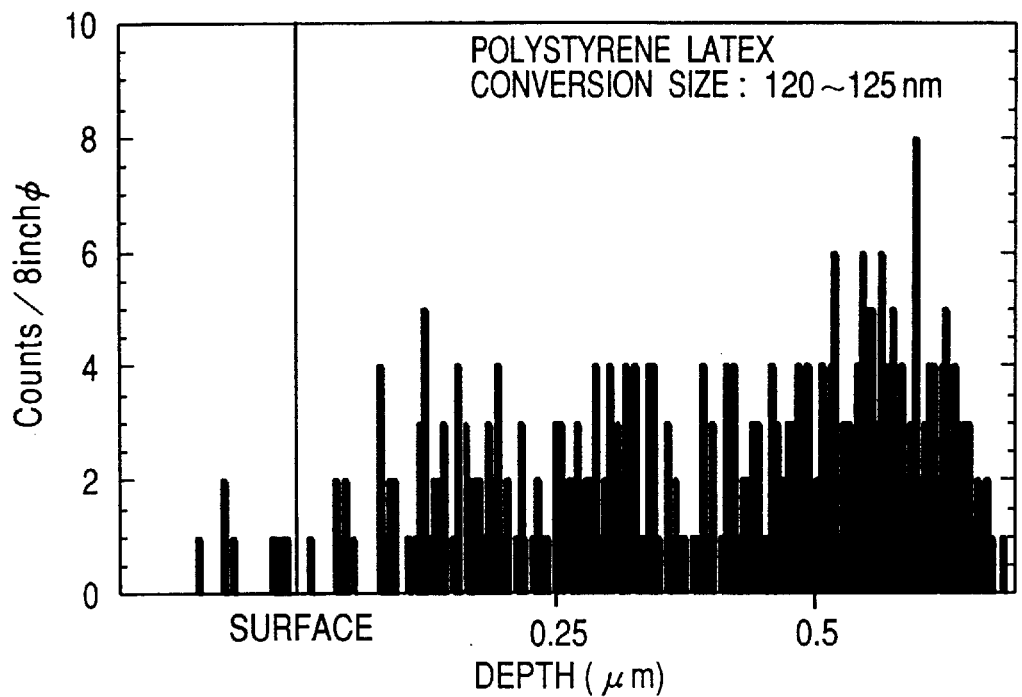
FIG. 15 is a diagram illustrating an example of displaying of depth distribution in a range wherein the defect size is greater than in FIG. 14.
Figure 16:
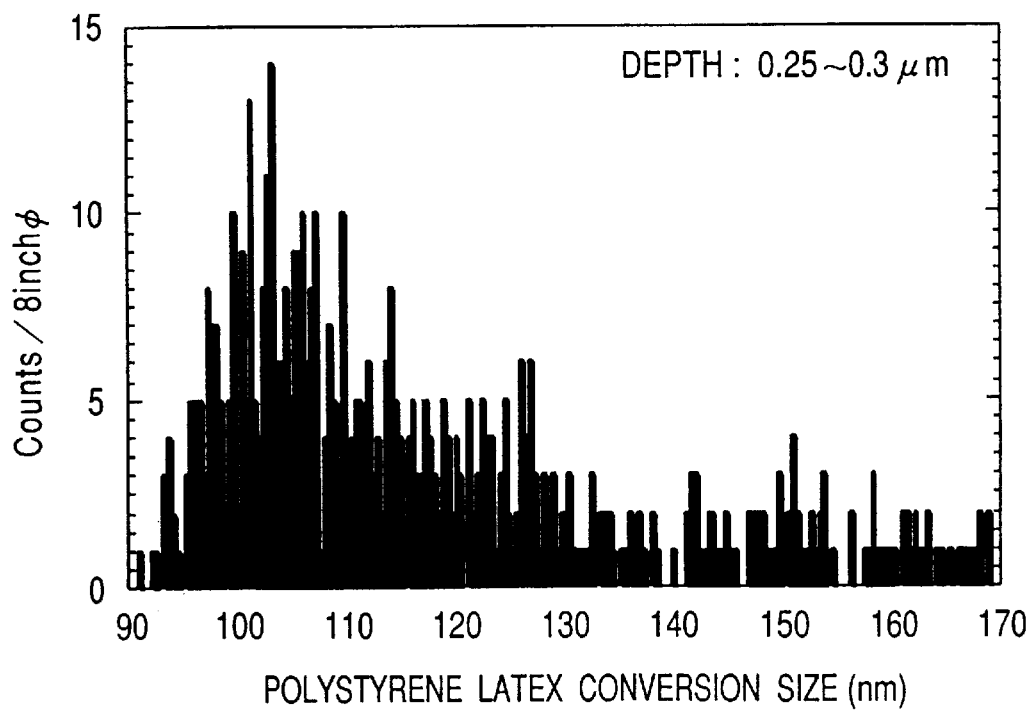
FIG. 16 is a diagram illustrating an example of displaying of grain size distribution in a limited depth position range in the plot of FIG. 11, FIG. 12 or FIG. 13.
Figure 17:
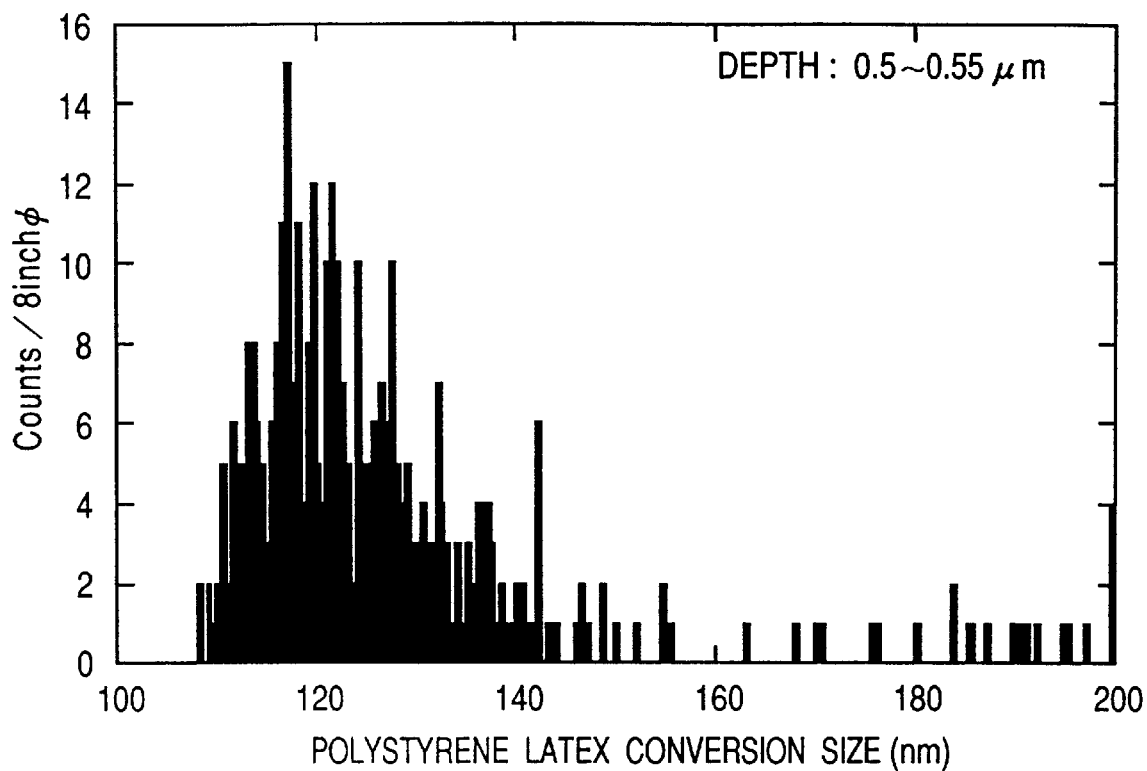
FIG. 17 is a diagram illustrating an example of displaying of grain size distribution in a range wherein the depth position is deeper than in FIG. 16.

Then, versions of the depth distribution in FIG. 11. 12 or 13 with the area limited by depth and size are FIGS. 14 and 15, while FIGS. 16 and 17 are versions of the grain size distribution similarly. Thus FIG. 14 shows, with respect to defects of 100 to 105 nm in size, the relationship between the defect depth (in $\mu$m) and the number of defects measured from an 8 inch wafer. FIG. 15 shows, with respect to defects of 120 to 125 nm in size, the relationship between the defect depth (in $\mu$m) and the number of defects measured from an 8 inch wafer. FIG. 16 shows, with respect to defects of 0.25 to 0.3 μm in depth position, the relationship between the defect size (in nm) and the number of defects measured from an 8 inch wafer. FIG. 17 shows, with respect to defects of 0.50 to 0.55 μm in depth position, the relationship between the defect size (in nm) and the number of defects measured from an 8 inch wafer.

Because of the relationships shown in FIGS. 14 and 15, the measurable and assessable depth range varies with the defect size and, by reason of those shown in FIGS. 16 and 17, the measurable and assessable defect size range varies with the depth at which measurement is done.

Figure 19:
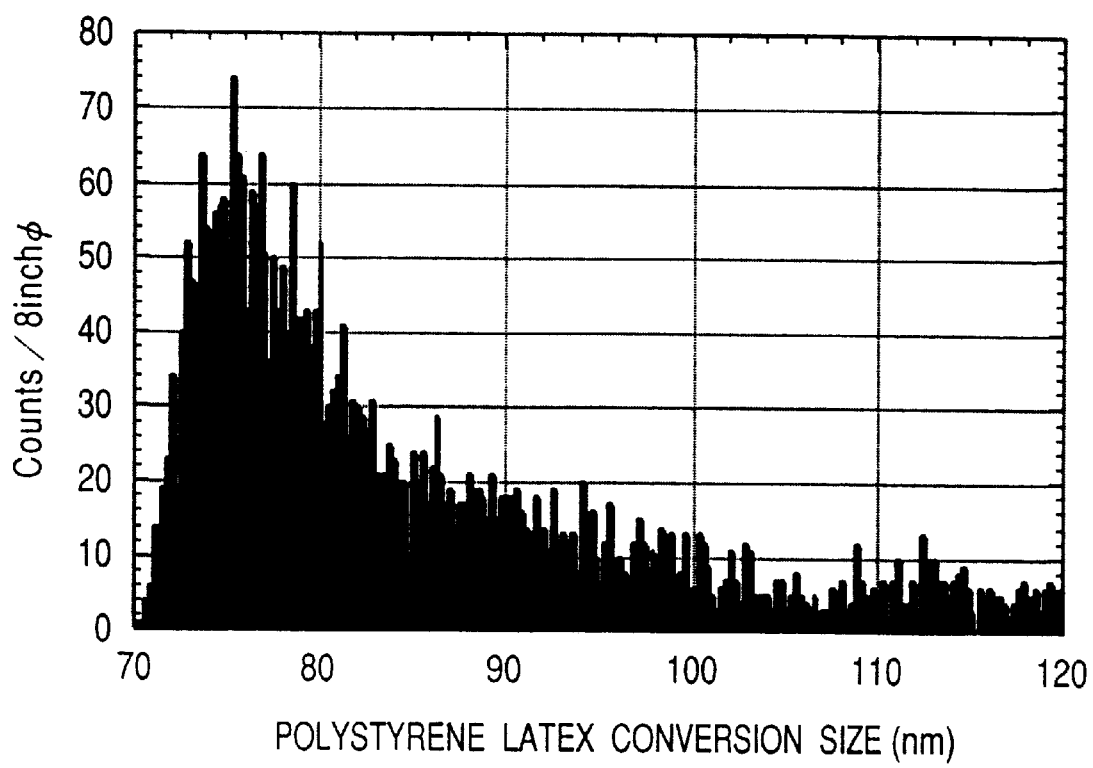
FIG. 19 is a diagram illustrating an example of displaying of defect grain size by the system of detection of foreign matter by the scattering of light of one wavelength according to the prior art.

FIG. 19 is a histogram illustrating as size distribution the distribution of the quantities equal to the sixth roots of the intensities of 532 nm scattered light from defects, and this corresponds to the distribution of grain sizes obtained when defects are detected with a conventional foreign matter checking apparatus for detecting scattered light of one wavelength absorbed by the samples. This distribution is observed as a distribution of the scattered light intensity attenuating effects of the size distribution and of the depth distribution of defects. When defects are to be measured by the scattering of light of a wavelength absorbable by the samples as in this case, separation of defect size and depth is indispensable. Measurement of defect size and depth separately from each other requires irradiating light rays of two wavelengths, of which one has a penetration depth at least three times as great as the other.

Conceivable examples of combination, for silicon wafer measurement, of irradiating wavelengths of which one has a penetration depth at least three times as great as the other include (λ1=352 nm and λ2=longer than 380 nm), (442 nm and longer than 500 nm), (488 nm and longer than 580 nm), (515 nm and longer than 620 nm) and (532 nm and longer than 650 nm). The combination of wavelengths should be altered according to the depth of measurement and the type of crystals to be measured. The present invention, for which a patent is applied, is not limited to silicon in its applicable substance, but can as well be applied to other materials (chemical compound semiconductors including GaAs, metals and organic materials). Where GaAs crystals are used for example, the wavelengths can be determined according to the penetration depth of each candidate wavelength. In this case, too, it is desirable to select wavelengths of whose λ1:λ2 ratio is at least 3:1. Preferably, the wavelengths should be determined similarly for other materials, too. In this manner, two dimensional displaying of grain size distribution as differentiated by depth is possible for other materials as well.

Figure 18:
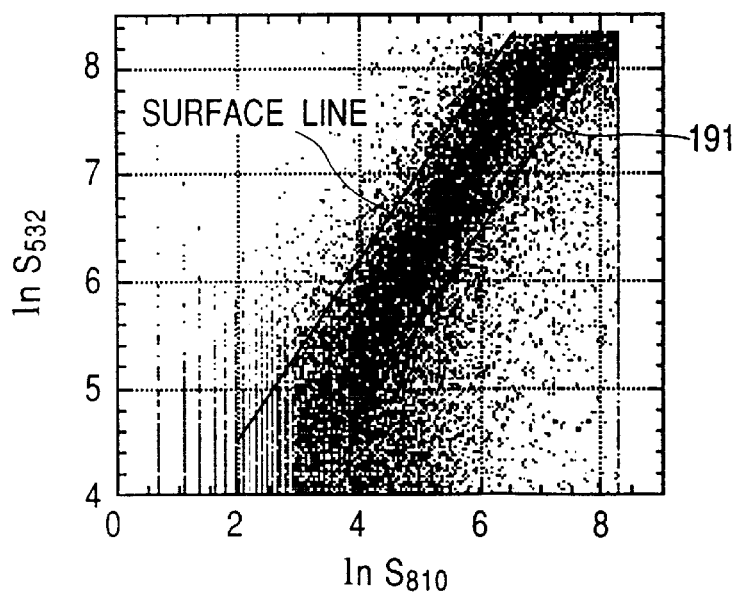
FIG. 18 is a diagram illustrating an example of displaying of defects in a wafer, wherein defects attributable to surface machining are present, by the system of Plot 1.

Next will be described the distinguishment between defects in a semiconductor wafer or the like attributable to machining such as surface polishing and defects within crystals. Research so far made has revealed that, in the representation of defect measurements in the form of depth distribution as differentiated by grain size, defects within crystals are substantially uniformly located in a deep area in a size distribution peculiar to crystal defects, but defects attributable to surface machining are distributed near the surface over a broader range of grain sizes than internal crystal defects. FIG. 18 is a graph displayed on the display unit 20 by the computer 17 by the system of Plot 1 (the first example), illustrating the intensities S1 and S2 of Rayleigh scattered light detected from a wafer having defects attributable to surface machining with irradiated light rays of wavelengths λ1 and λ2, respectively. It is seen that, because the wafer has defects attributable to surface machining, such defects are distributed near the surface over a broad range of grain sizes at a higher density than internal defects are. Therefore, the computer 17 sets a threshold 191 for both defect size distribution and defect density distribution within a certain shallow depth, and enables the measuring person to judge whether or not a given sample surpasses that threshold 191 by displaying the threshold 191 on the screen of the display unit 20, and to determine these defects to have derived from surface machining. The computer 17 also sets the threshold 191 for both defect size distribution and defect density within a certain shallow depth, computes the depth distribution surpassing that threshold as differentiated by grain size, and enables the measuring person to determine given defects to have derived from surface machining by two-dimensionally displaying the distribution on the screen of the display unit 20. The computer 17 can as well set the threshold 191 for both defect size distribution and defect density within a certain shallow depth, compute the depth distribution surpassing that threshold as differentiated by grain size, extract information regarding defects attributable to surface machining from the computed depth distribution surpassing that threshold as differentiated by grain size, and supply that information to the display unit 20.

The present invention provides the effect of making possible depth distribution of defects in a semiconductor wafer or the like as differentiated by size, thereby enabling defects attributable to surface machining and internal defects to be separately measured and assessed.

The invention also provides the effect of making possible depth distribution of defects in a semiconductor wafer or the like as differentiated by size, thereby enabling crystal defects arising within the semiconductor wafer and other defects to be separately measured and assessed.

The invention further provides the effect of making it possible to measure and assess crystal defects occurring in a depth of up to about 0.5 μm in a semiconductor substrate, such as a silicon wafer, in terms of relationship between size and depth, prevent an LSI semiconductor onto a faulty substrate as a result, and thereby enhance the yield of LSI semiconductors and their reliability as semiconductors.

The invention moreover provides the effect of making it possible to reveal the size-depth relationship of defects, assess in detail troublesome defects including those within the sample (solid) when manufacturing LSI semiconductors, facilitate the identification of the cause for the fault, if any, in the sample, take a prompt remedy easily, and thereby significantly enhance the yield of samples.

What is claimed is:

1. An apparatus for assessing any defect within a solid by irradiating the surface of the solid with light rays of a plurality of wavelengths and detecting scattered light from any defect at least in that solid, provided with:

irradiating optical systems for irradiating with light rays of at least two different wavelengths differing in the depth of penetration into said solid;

a detecting optical system for detecting the intensity of scattered light from a defect generated by a shorter wavelength one of the light rays of at least two different wavelengths emitted from the irradiating optical systems, and that of scattered light from the defect generated by a longer wavelength one of same;

a calculating means for figuring out, from the scattered light intensity deriving from said shorter wavelength ray and that deriving from said longer wavelength ray, both detected by said detecting optical system, a value corresponding to a defect size and another value corresponding to a defect depth; and a display means for displaying a distribution revealing the relationship between said defect size and said defect depth and wherein the detectable depth in said distribution depends on said defect size.

2. An apparatus for assessing any defect within a solid by irradiating the surface of the solid with light rays of a plurality of wavelengths and detecting scattered light from any defect at least in that solid, provided with:

irradiating optical systems for irradiating with light rays of at least two different wavelengths differing in the depth of penetration into said solid;

a detecting optical system for detecting the intensity of scattered light from a defect generated by a shorter wavelength one of the light rays of at least two different wavelengths emitted from the irradiating optical systems, and that of scattered light from the defect generated by a longer wavelength one of same;

a calculating means for figuring out, from the scattered light intensity deriving from said shorter wavelength ray and that deriving from said longer wavelength ray, both detected by said detecting optical system, a value corresponding to a defect size and another value corresponding to a defect depth; and a display means for displaying a depth distribution as differentiated by defect size on the basis of the value corresponding to the defect size and the value corresponding to the defect depth, both figured out by the calculating means.

3. An apparatus for assessing any defect within a solid by irradiating the surface of the solid with light rays of a plurality of wavelengths and detecting scattered light from any defect at least in that solid, provided with:

irradiating optical systems for irradiating with light rays of at least two different wavelengths differing in the depth of penetration into said solid;

a detecting optical system for detecting the intensity of scattered light from a defect generated by a shorter wavelength one of the light rays of at least two different wavelengths emitted from the irradiating optical systems, and that of scattered light from the defect generated by a longer wavelength one of same;

a calculating means for figuring out, from the scattered light intensity deriving from said shorter wavelength ray and that deriving from said longer wavelength ray, both detected by said detecting optical system, a two-dimensional distribution; and a display means for displaying a distribution revealing the relationship between said defect size and said defect depth on the basis of the two-dimensional distribution figured out by the calculating means.

4. An apparatus for assessing any defect within a solid by irradiating the surface of the solid with light rays of a plurality of wavelengths and detecting scattered light from any defect at least in that solid, provided with:

irradiating optical systems for irradiating with light rays of at least two different wavelengths differing in the depth of penetration into said solid;

a detecting optical system for detecting the intensity of scattered light from a defect generated by a shorter wavelength one of the light rays of at least two different wavelengths emitted from the irradiating optical systems, and that of scattered light from the defect generated by a longer wavelength one of same;

a calculating means for figuring out, from the scattered light intensity deriving from said shorter wavelength ray and that deriving from said longer wavelength ray, both detected by said detecting optical system, a two-dimensional distribution; and a display means for displaying a depth distribution as differentiated by defect size on the basis of the two-dimensional distribution figured out by the calculating means.

5. An apparatus for defect assessment, as claimed in claim 1, wherein the depth of penetration of said longer wavelength in said solid is three times as great in the depth penetration of said shorter wavelength in said solid.

6. An apparatus for defect assessment, as claimed in claim 1, in whose display means a defect distribution is displayed in which values proportional to the logarithm of the scattered light intensity deriving from the longer wavelength are plotted on the X axis and values proportional to the logarithm of the scattered light intensity deriving from the shorter wavelength from the defect are plotted on the Y axis.

7. An apparatus for defect assessment, as claimed in claim 1, in whose display means a defect distribution is displayed in which values proportional to the sixth root of the scattered light intensity deriving from the longer wavelength are plotted on the X axis and values proportional to the logarithm of the scattered light intensity deriving from the shorter wavelength from the defect are plotted on the Y axis.

8. An apparatus for defect assessment, as claimed in claim 1, in whose display means a defect distribution is displayed in which values proportional to the sixth root of the scattered light intensity deriving from the longer wavelength are plotted on the X axis and the Logarithms of their ratios to the scattered light intensity deriving from the shorter wavelength from the defect are plotted on the Y axis.

9. An apparatus for assessing any defect within a solid comprising:

means for irradiating a surface of the solid with light absorbable by the solid;

means for measuring resultant scattered light such that depth of defects are derived as differentiated by defect size; and means for displaying results.

* * * * *